United States Patent [19]

Fisher

[11] Patent Number: 4,791,287
[45] Date of Patent: Dec. 13, 1988

[54] APPARATUS AND AN ASSOCIATED METHOD FOR DETECTING HAZE OR PEARLESCENCE IN CONTAINERS

[75] Inventor: Edward J. Fisher, Library, Pa.

[73] Assignee: American Glass Research, Inc., Butler, Pa.

[21] Appl. No.: 125,936

[22] Filed: Nov. 27, 1987

[51] Int. Cl.$^4$ ............................................. B07C 5/342
[52] U.S. Cl. ................................. 250/223 B; 356/240; 356/428
[58] Field of Search ..................... 250/571, 223 B, 572; 356/239, 240, 428; 358/106; 209/524, 526

[56] References Cited

U.S. PATENT DOCUMENTS

| | | | |
|---|---|---|---|
| 3,202,826 | 8/1965 | Greathouse | 250/218 |
| 3,886,356 | 5/1975 | Gomm et al. | 250/223 B |
| 3,894,806 | 7/1975 | Remy et al. | 356/240 |
| 4,027,973 | 6/1977 | Kaye | 356/73 |
| 4,338,028 | 7/1982 | Tailleur et al. | 356/240 |
| 4,584,469 | 4/1986 | Lovalenti | 250/223 B |

Primary Examiner—Edward P. Westin
Assistant Examiner—Charles F. Wieland
Attorney, Agent, or Firm—Arnold B. Silverman

[57] ABSTRACT

Apparatus and an associated method for inspecting translucent containers to determine whether haze or pearlescence exists include a light source and associated photodetectors which are in spaced relationship to permit passage of containers to be inspected therebetween. A processing unit determines whether a particular predetermined linear array of photodetectors has been illuminated to indicate the presence of pearlescence, whether a conical light beam has illuminated a circular array to indicate the presence of haze or whether neither defect exists. In a preferred embodiment, individual portions of the container less than the full circumference are tested with the results being cumulatively determined so as to minimize the likelihood that minor defects will provide a false reading of the presence of either haze or pearlescence. Counters, which are preferably electronic in nature to afford adequate speed of response may be used to total separately the number of sensors illuminated in the haze category, pearlescence category or no defect category and a comparison made to determine which of the characteristics exist for a particular container.

21 Claims, 2 Drawing Sheets

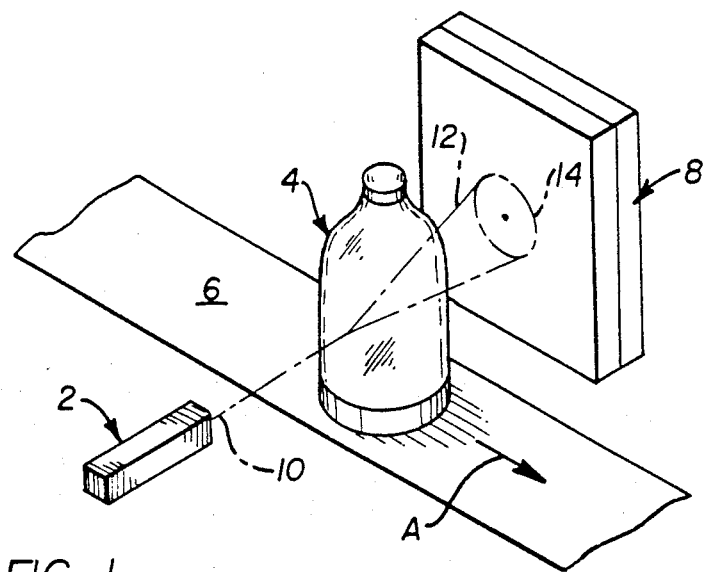
FIG. 1
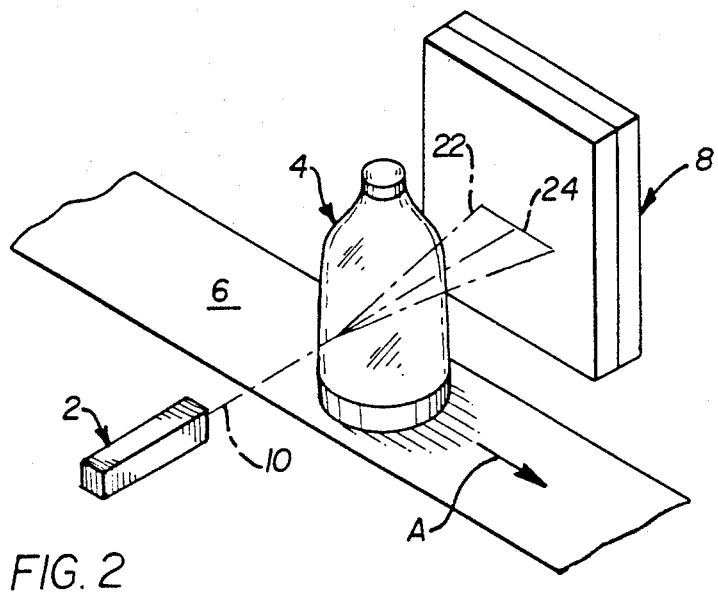
FIG. 2
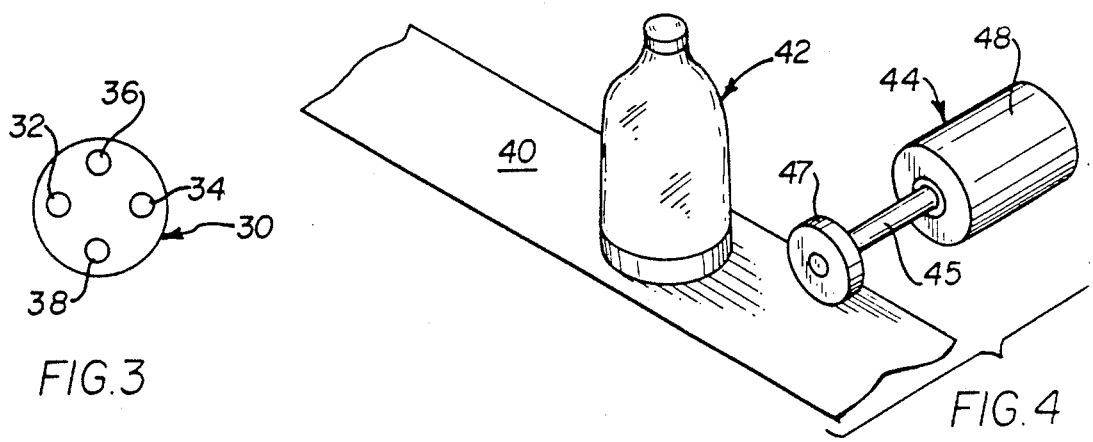
FIG. 3
FIG. 4

APPARATUS AND AN ASSOCIATED METHOD FOR DETECTING HAZE OR PEARLESCENCE IN CONTAINERS

BACKGROUND OF THE INVENTION

1. Field Of The Invention

This invention relates to an apparatus and an associated method for optical inspection of translucent containers in order to determine whether haze or pearlescence is present.

2. Description Of The Prior Art

It has been known to effect automated inspection of translucent containers for a wide variety of departures from specifications in an automated manner. It has been known to employ a light source on one side of the container and cooperating detectors on the other side of the container in order to ascertain whether certain defects exist in the container. See generally, U.S. Pat. Nos. 3,886,356; 3,894,806; 4,338,028; and 4,584,469.

U.S. Pat. No. 3,886,356 discloses the use of three detectors which cooperate with a light source in attempting to determine whether perturbations have been formed in the container.

U.S. Pat. No. 3,894,806 discloses introduction of light into a container opening to illuminate the container interior and employ externally exposed detectors for the presence of imperfections or impurities.

U.S. Pat. No. 4,338,028 discloses inspection of translucent containers by means of light and an array of photosensitive devices disposed behind a screen.

U.S. Pat. No. 4,584,469 discloses inspection of translucent containers by means of light and associated detectors wherein radial reflective defects are monitored by the angles at which light emerges.

In spite of the foregoing prior art disclosures, there is lacking in the art an effective apparatus and method for automated inspection of translucent containers in order to determine whether either haze or pearlescence is present.

SUMMARY OF THE INVENTION

The present invention has met the above-described need.

The apparatus, in its preferred embodiments, provides light source means for directing a beam of collimated light onto the container. Photodetector means are disposed in spaced relationship with respect to the light source means to permit passage of a container therebetween and are adapted to receive light passing through the container. The photodetector means includes a photodetector array having detectors positioned to detect a light pattern corresponding to a container having haze and detectors to detect a light pattern corresponding to a container with pearlescence. Processing means receive output signals from the photodetector means. This permits the apparatus to provide output regarding whether haze exists, pearlescence exists or neither of these defects exists.

In general, the pearlescence detectors will be a linear array and the haze detectors will be a circular array adapted to receive a conical beam of light. In a preferred embodiment at least some of the detectors in the pearlescence detecting array will also be in the haze detecting array.

The processing means preferably have counters for accumulating output signals and determining the quantity of each signal received indicating haze or indicating pearlescence. By comparing the count on the counters, a determination may be made regarding the existence of either of these defects in a particular container. In a preferred embodiment, the processing means has AND gates cooperating with the counters.

In a preferred embodiment points on the circumference of the containers are independently tested with sequential testing resulting in cumulative counting of the output. A shaft encoder may be employed to coordinate the determination of positions of the individual tests.

The method, in its preferred form, is patterned after the described apparatus.

It is an object of the present invention to provide apparatus and a method for automatically inspecting translucent containers to determine whether either pearlescence or haze is present in these containers.

It is a further object of the present invention to employ a collimated light beam and detectors of the photodetector type which are adapted to provide electrical output signals corresponding to the patterns of light received by the detectors with determination of the existence of the two defects being made through processing means.

It is a further object of the present invention to provide such a system wherein specific settings of threshold determinants of each category of defect may be provided and relative comparative means may also be provided to establish a quantitative relationship between the extent to which haze and pearlescence exist.

It is a further object of the present invention to provide such a system which is reliable and economical to manufacture and use.

It is a further object of the invention to provide such a system which is adapted for use with a wide variety of translucent container materials and container sizes.

These and other objects of the invention will be more fully understood from the following description of the invention on reference to the illustrations appended hereto.

BRIEF DESCRIPTION OF THE DRAWINGS

FIG. 1 is a schematic illustration of an embodiment of the invention showing a hazy container.

FIG. 2 is a schematic illustration of the invention showing a pearlescent container.

FIG. 3 is a schematic illustration of a form of photodetector system usable in the present invention.

FIG. 4 is a schematic illustration of a conveyor system and associated apparatus for use in examining portions of a container at a time.

DESCRIPTION OF THE PREFERRED EMBODIMENTS

Figure 5:
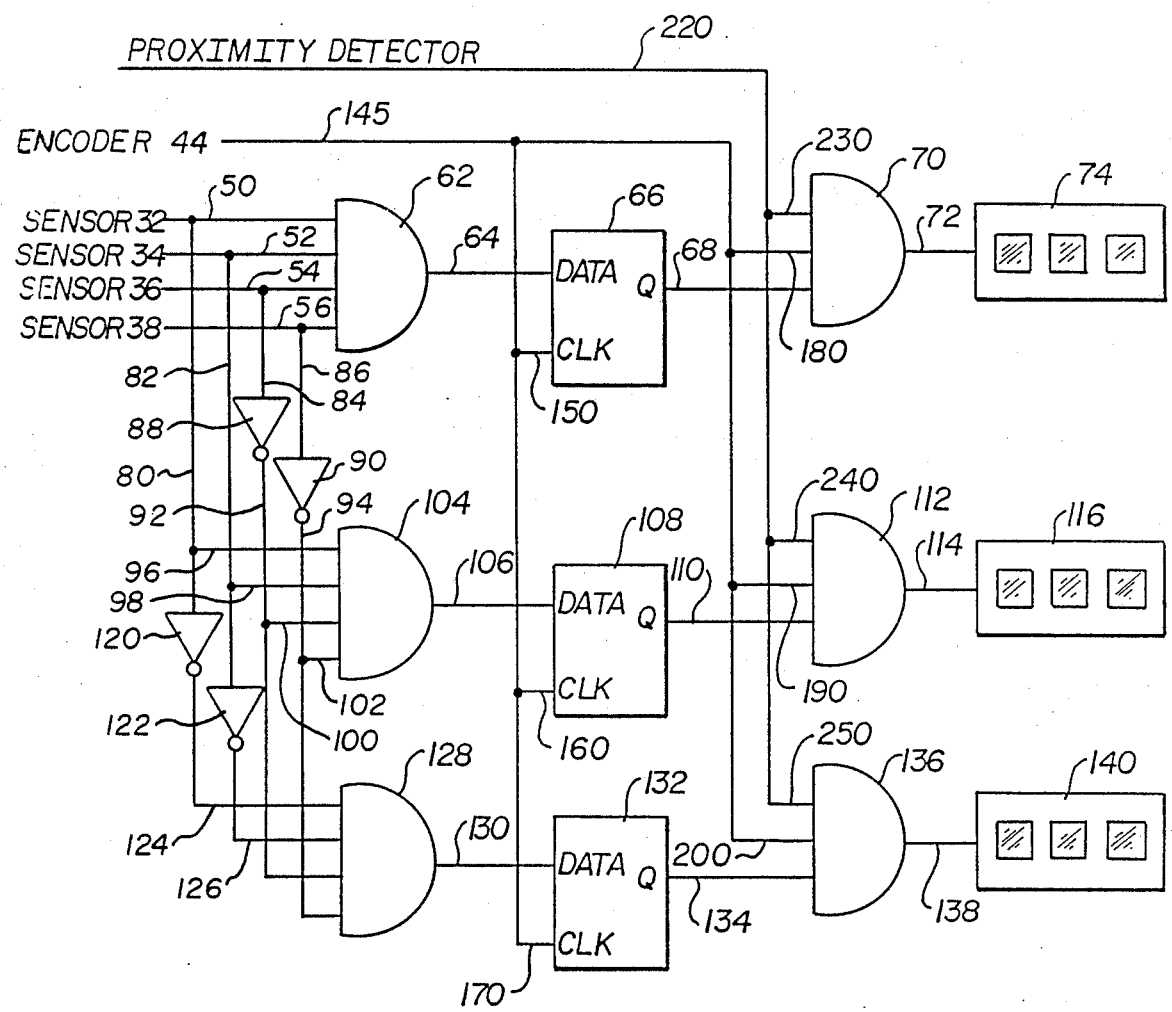
FIG. 5 is a schematic illustration of a form of processing means usable in the present invention.

As used herein, unless in a particular usage a clear indication to the contrary is expressly provided, the term "translucent container" shall mean containers which are composed of a material which permits light transfer therethrough or have portions which are being inspected which permit light passage therethrough regardless of whether the containers are clear or tinted and expressly includes but is not limited to containers made of resinous plastic materials.

Referring more specifically to FIG. 1, there is shown light source means 2 for directing a beam of collimated light 10 onto the container 4. The light source means may be of any suitable form such as a laser, for example, although neither the single wavelength nor the coherence is required. It is preferred that the light beam be of relatively small diameter on the order of less than about 0.05 inch and that collimation be about 5 millirad. The light wavelength should be such that the container is transparent with respect to the wavelength. An LED or incandescent source could be employed if adequately collimated.

As is shown in FIG. 1 a translucent container 4 has a generally flat bottom and has its longitudinal axis vertically oriented. It is moving with conveyor 6 in the direction indicated by the arrow A. The light beam 10 emerging from light source means 2 passes through container 4 and in the instance illustrated which is a hazy container emits a conical light beam 12 which impinges upon photodetector means 8. The photodetectors in the haze detecting array 14 are in the form shown arranged in a generally circular path. The array 14 will receive light in those regions corresponding to the existence of the defective hazy container and, in a manner to be discussed hereinafter, will provide an indication that this defect exists.

With respect to certain types of plastic, such as polyethylene terephthalate, for example, if the plastic is too hot during the molding process, haziness will occur and if the plastic is too cold during the molding process, pearlescence (sometimes referred to as "whitening") will occur. These defects can cause the containers to become commercially unacceptable primarily for aesthetic reasons. The apparatus and method of the present invention not only enable the manufacturer to obtain automated inspection, but also can determine whether the defect is haze or pearlescence and thereby give information which can permit an operator to effect adjustment of the temperature in the proper direction. If desired, this information may be so provided as to effect a servo type automatic adjustment.

With reference to FIG. 2, one of the distinct advantages of the present invention is that it is able to not only detect the presence of haze or pearlescence but distinguish between the two defects. It will be appreciated as the temperature adjustment for one type of defect is in the opposite direction than the adjustment for the other, this ability to discern the distinction between the two types of defects is very important.

In FIG. 2, the beam 10 impinges on the container sidewall and emits a planar beam 22 which results in a linear light pattern impinging on the linear photodetector array 24 which may be a linear array of photodiodes, for example. It will be appreciated, therefore, that a first array 14 of detectors within the photodetecting means 8 will be energized by light in the case of haze as in FIG. 1. This results from the conical beam 12 producing a circular light pattern on array 14 on the photodetector means 8. The beam 22 which results when pearlescence exists produces the linear pattern on array 24. The sensors which are illuminated in line 24 may, at least in part, form a part of the sensors which are illuminated by circular pattern 14. The photodetector means 8 which will be discussed in greater detail hereinafter provide a first photodetector array which has photodetectors illuminated by light pattern 12 and a second photodetector array which may include some of the photodetectors in the array in circular array 14 which will be illuminated by light pattern 22. In this manner, by determining which photodetectors have received the appropriate amount of light, one can determine whether haze or pearlescence exists. In the event that neither photodetector array 14 or photodetector array 24 is illuminated to a level corresponding to the presence, respectively, of haze or pearlescence during a period when a container is known to be present then the container has neither defect.

Referring to FIG. 3 a simplified illustration of the concepts of FIGS. 1 and 2 showing a unit employing a few photodetectors will be considered. Assuming that the circle 30 of the photodetector means corresponds to the array 14 in a general manner, in the event that haze exists in light pattern 12 of FIG. 1 impinges on the photodetector means 8, all of the sensors 32, 34, 36, 38 will receive sufficient light as to emit a corresponding output signal. Assuming, however, that pearlescence exists solely, photodetectors 32 and 34 will be illuminated and corresponding output signals will emerge.

It is preferred that the photodetectors have the capability of providing a suitable electrical output signal response to receipt of light passing through the translucent container so as to provide a detailed indication regarding whether a defect exists and if it does as to whether it is haze or pearlescence. Among the preferred types of photodetectors are photodiodes and phototransistors. Referring to FIG. 4 there is shown a conveyor 40 which is transporting a container 42. In this embodiment of the invention, it is contemplated that only a relatively small portion of the circumference will be tested in the manner illustrated in FIGS. 1 through 3 at a given instance and sequentially several points on the circumference will be tested so as to preferably approximate the entire diameter. In order to assist with coordination of the container position with respect to the data generated by the test system, a shaft encoder 44 is employed. Wheel 47, which is connected by shaft 45 to unit 48, contacts conveyor 40 so as to rotate responsive to conveyor movement. As the conveyor moves and the container advances, the shaft encoder provides an electrical output signal which facilitates coordinating data received by photodetectors with the processing means indication as to the nature of the container and whether one of the two defects exists.

Referring to FIG. 5, the processor means which provide a preferred means of processing the output signals from the photodetectors to permit determination as to whether haze, pearlescence or neither of these defects exist. The electrical output signals from sensors 32, 34, 36, 38, respectively, are carried by leads 50, 52, 54, 56 to AND gate 62. If all the inputs are TRUE, representing illumination of all the photodetectors, the output of the AND gate 62 is also TRUE. Lead 64 carries this signal to the DATA input of latch 66. The signal from the encoder 44 is carried over lead 145 and 150 to the CLOCK input of latch 66. When the CLOCK input goes TRUE, the Q output of latch 66 goes TRUE also (if DATA is TRUE), and the Q output stays TRUE while the CLOCK input is TRUE (regardless of the state of DATA). The output of latch 66 is carried over lead 68 to AND gate 70. The signal from the encoder 44 is carried over lead 145 and lead 180 to another input of AND gate 70. The signal from a sensor (not shown) which senses the presence of a container in the light beam 10 (of FIGS. 1 and 2) is carried over leads 220 and 230 to the third input of AND gate 70. The output of AND gate 70 will be TRUE only if all three inputs are TRUE, namely that all four sensors are TRUE, the detector sensing the presence of a container is TRUE and the encoder output is TRUE. The output of AND gate 70 is carried over lead 72 to counter 74. It will be appreciated that this arrangement of gates, latches and counters performs the function of counting encoder pulses only when a container is present in the light beam 5 and only when the output of all four sensors are true when the encoder goes TRUE. Thus, this counter is the haze counter which indicates the number of times that illumination of all four sensors 32, 34, 36, 38 (FIG. 3) occurs thereby indicating that a haze defect exists.

The signals from leads 50, 52, 54, 56 are delivered to leads 80, 82, 84, 86, respectively. Leads 84 and 86 deliver signals to logic inverters 88 and 90, respectively. The inverters deliver signals on leads 92, 100 and 94, 102, respectively, to AND gate 104. Also signals from leads 80 and 82 are carried on leads 96 and 98, respectively, to AND gate 104. The output of AND gate 104 will be TRUE when signals from sensors 32 and 34 are TRUE and when signals from sensors 36 and 38 are NOT TRUE (because of the inverters 88 and 90). The output signal of AND gate 104 is delivered by lead 106 to the DATA input of latch 108. The signal from the encoder 44 is carried over leds 145 and 160 to the CLOCK input of latch 108. When the CLOCK input goes TRUE, the Q output of latch 108 goes TRUE also (if DATA is TRUE), and the Q output stays true while the CLOCK input is TRUE (regardless of the state of DATA). The output of latch 108 is carried on lead 110 to AND gate 112. The signal from the encoder 44 is carried over leads 145 and 190 to another input of AND gate 112. The signal from a sensor (not shown) which senses the presence of a container in the light beam 10 (of FIGS. 1 and 2) is carried over leads 220 and 240 to the third input of AND gate 112. The output of AND gate 112 will be TRUE only if all three inputs are TRUE, namely that the output of the latch 110 is TRUE, the encoder output is TRUE and the detector sensing the presence of a container is TRUE. The output of AND gate 112 is carried over lead 114 to counter 116. It will be appreciated that the counter will count encoder pulses only when a container is present and only when the horizontal sensors 32 and 34 (of FIG. 3) are TRUE (illuminated) and the vertical sensors 36 and 38 (of FIG. 3) are NOT TRUE (not illuminated) when the encoder goes TRUE. Thus, this counter is the pearlescence counter which indicates the number of times that only the horizontal sensors are illuminated thereby indicating that a pearlescence defect exists.

The signals from leads 80 and 82 are delivered to inverters 120 and 122, respectively. The output signals from these inverters are delivered by leads 124 and 126, respectively, to the AND gate 128. Leads 92 and 94 deliver signals to AND gate 128 as well. The output of AND gate 128 will be TRUE when signals from sensors 32, 34, 36, 38 are NOT TRUE (because of inverters 120, 122, 88, 90, respectively). The output signal of AND gate 128 is delivered by lead 130 to the DATA input of latch 132. If DATA is TRUE, the Q output of latch 132 goes TRUE when the encoder 44 outputs a signal by way of leads 145 and 170 and, due to the action of the latch, stays TRUE while the encoder is TRUE regardless of whether DATA stays TRUE or not. The Q output of latch 132 is delivered by lead 134 to AND gate 136. The signal from the encoder 44 is carried over leads 145 and 200 to another input of AND gate 136. The signal from a sensor (not shown) which senses the presence of a container in the light beam 10 (FIGS. 1 and 2) is carried over leads 220 and 250 to the third input of AND gate 136. The output of AND gate 136 will be TRUE only if all three inputs are TRUE, namely that the output of latch 132 is TRUE, the encoder output is TRUE and the detector sensing the presence of a container is TRUE. The output of AND gate 136 is carried over lead 138 to counter 140. It will be appreciated that counter 140 will count encoder pulses only when a container is present and only when all four sensors 32, 34, 36, 38 (FIG. 3) are NOT TRUE (that is not illuminated) when the encoder goes TRUE. Thus, this counter is the no defect counter.

In instances where it is contemplated that a plurality of individual segments of the container perimeter will be tested separately, as is preferred, and the cumulative count on counters 74, 116, 140 will be employed to determine whether haze or pearlescence or no defect of this type exists, and the output of encoder 44 will be employed in each latch 66, 108, 132. In general, the counter 74, 116, 140 with the highest total will indicate the predominant activity with respect to the sensors. With respect to each counter when a predetermined threshold level indicating the presence of haze or pearlescence or no defect has been exceeded this will be the conclusion reached with regard to the test of the particular container.

It will be appreciated that in the method of the present invention, detection of haze or pearlescence in a translucent container may be accomplished. By providing the light source means on one side of the path of movement of the containers and cooperating photodetector means on the other side of the path to receive light passing through the containers, one may be correlating which photodetectors have been illuminated determine whether haze exists, whether pearlescence exists or whether no defect exists. In general, a linear array of photodetectors will be illuminated when pearlescence is present in the container and a circular array will be illuminated when haze exists. In a preferred embodiment small areas of the container perimeter are sequentially scanned and the output in respect of the three options is cumulatively monitored in order to determine which condition or conditions exist. In general, it is preferred to effect the testing over about 20% to 40% of the perimeter of the container.

The output of the sensors of interest and the responsive counter tallies are compared in reaching a determination as to whether haze, pearlescence or neither defect exists.

It will be appreciated, therefore, that the present invention provides an effective means for inspecting a container to determine whether either haze or pearlescence exists and to distinguish between the two defects so that an indication of which defect exists is provided. All of this is accomplished in an automated fashion which may employ segmented analysis of a portion of the circumference of the container followed by similar analysis of other portions of the circumference with cumulative processing of the responsive output signals. All of this is accomplished in a reliable, economical and efficient manner.

While the system disclosed herein emphasizes a container being translated by the inspection apparatus, other approaches may be employed while obtaining the benefit of the present invention. For example, the conveyor may transport the container to a position aligned with the inspection apparatus, where the container translation would be stopped and the container axially rotated during inspection thereof.

It will be appreciated that while for simplicity of disclosure herein has centered around inspection of the container at a single location, it will be appreciated that the invention is not so limited. Multiple inspection units at different elevations or a single inspection movable to different elevations may be employed, if desired. While haze is generally uniformly distributed throughout the container, pearlescence appears to occur first in a limited location and then spreads to other portions of the container.

Whereas particular embodiments of the invention have been described above for purposes of illustration, it will be evident that those skilled in the art, that numerous variations of the details may be made without departing from the invention as defined in the appended claims.

I claim:

1. Apparatus for detecting defects in a translucent container comprising
    light source means for directing a beam of light onto said container,
    photodetector means for receiving light passing through said container and being spaced from said light source means,
    said photodetector means including a photodetector array having detectors positioned to detect a light pattern corresponding to a container with haze and detectors positioned to detect a light pattern corresponding to a container with pearlescence, and
    processing means for receiving output signals from said photodetector means, whereby said apparatus determines whether haze or pearlescence exists in said container.

2. The detecting apparatus of claim 1 including
    said photodetectors for detecting pearlescence being a linear array.

3. The detecting apparatus of claim 2 including
    said photodetectors for detecting haze being positioned to receive at least portions of a conical beam of light.

4. The detecting apparatus of claim 3 including
    some of said photodetectors for detecting pearlescence also serving to detect haze.

5. The detecting apparatus of claim 3 including
    said light source means having means for creating said beam as collimated light, and
    said processing means having counter means for determining from said photodetector means output signals whether haze, pearlescence or neither of these effects exist within a container.

6. The detecting apparatus of claim 5 including
    said counter means having
    a first counter for computing the number of said output signals received from said photodetectors employed to determine whether haze exists in said container,
    a second coutner for computing the number of said output signals received from said photodetectors employed to determine whether pearlescence exists, and
    a third counter for indicating the absence of output signals from said photodetectors to indicate that neither said defect exists.

7. The detecting apparatus of claim 6 including
    said processing means as to each said counter having AND gates for emitting a pulse to its associated counter only when a predetermined group of said photodetectors have emitted a signal, and
    means within each said counter for increasing its count by one when it receives a signal from its associated AND gate.

8. The detecting apparatus of claim 5 including
    said apparatus of such size as to inspect only a portion of the circumference of a said container at one time,
    coordinating means for providing a position signal corresponding to the container position with respect to said light source means and said photodetector means, and
    said processing means having means for determining the cumulative count of said output signals from all portions of said container which have been inspected, whereby minor defects will not be interpreted by said apparatus as being haze or pearlescence.

9. The detecting apparatus of claim 8 including
    said coordinating means being a shaft encoder.

10. The detecting apparatus of claim 9 including
    the height of said photodetector arrays being less than the height of said containers.

11. A method for detecting haze or pearlescence in a translucent container comprising
    providing light source means for emitting a light beam disposed on one side of a path of movement of said containers and cooperating photodetector means disposed on the other side of said path to receive light passing through said containers,
    positioning a container between said light source means and said photodetector means,
    determining if a first predetermined group of photodetectors corresponding to a pearlescent container have emitting output signals,
    determining if a second predetermined group of photodetectors corresponding to a hazy container have emitted output signals, whereby a determination of whether haze or pearlescence or neither exist in said container can be made.

12. The method of claim 11 including
    employing a linear array of photodetectors as said first predetermined group of photodetectors.

13. The method of claim 12 including
    employing a generally circular planar array for receiving a conical beam of light as said second predetermined group of photodetectors.

14. The method of claim 13 including
    counting the output of said first array,
    counting the output of said second array, and
    effecting a comparison of the outputs of said two arrays.

15. The method of claim 14 including
    counting the number of times that neither said first nor said second predetermined groups of photodetectors have an output, whereby the absence of haze or pearlescence may be monitored.

16. The method of claim 14 including
    effecting said testing over only a portion of the circumference of said container at one time,
    sequentially testing one or more additional portions of said container, and
    totalling the count of output signals emitted in each sector prior to effecting said comparison.

17. The method of claim 16 including
    effecting said testing on about 20% to 40% of the circumference of said container, whereby minor optical discontinuities in said container will not create false readings of the presence of either haze or pearlescence.

18. The method of claim 17 including effecting said testing on the container composed of a synthetic resinous material.

19. The method of claim 18 including effecting said testing on a container composed of polyethylene terephthalate.

20. The method of claim 14 including emitting said light beam as a collimated light beam.

21. The method of claim 17 including effecting said testing on a generally cylindrical container.